US010351890B2

(12) United States Patent
Lee et al.

(10) Patent No.: US 10,351,890 B2
(45) Date of Patent: Jul. 16, 2019

(54) METHOD FOR PREPARING RECOMBINANT PROTEINS THROUGH REDUCTION OF RNPA GENE EXPRESSION

(71) Applicant: KOREA ADVANCED INSTITUTE OF SCIENCE AND TECHNOLOGY, Daejeon (KR)

(72) Inventors: Sang Yup Lee, Daejeon (KR); Hannah Chung, Daejeon (KR)

(73) Assignee: MEDICOSBIOTECH, INC., Seoul (KR)

( * ) Notice: Subject to any disclaimer, the term of this patent is extended or adjusted under 35 U.S.C. 154(b) by 0 days.

(21) Appl. No.: 15/533,273

(22) PCT Filed: Dec. 9, 2015

(86) PCT No.: PCT/KR2015/013419
§ 371 (c)(1),
(2) Date: Jun. 5, 2017

(87) PCT Pub. No.: WO2016/093606
PCT Pub. Date: Jun. 16, 2016

(65) Prior Publication Data
US 2017/0342454 A1    Nov. 30, 2017

(30) Foreign Application Priority Data

Dec. 9, 2014  (KR) ................ 10-2014-0175780
Dec. 9, 2015  (KR) ................ 10-2015-0174828

(51) Int. Cl.
*C12P 21/00*   (2006.01)
*A61K 39/00*   (2006.01)
*C12N 15/113*  (2010.01)

(52) U.S. Cl.
CPC .......... *C12P 21/00* (2013.01); *C12N 15/1137* (2013.01); *C12Y 301/26005* (2013.01); *C12N 2310/14* (2013.01); *C12N 2330/50* (2013.01)

(58) Field of Classification Search
None
See application file for complete search history.

(56) References Cited

U.S. PATENT DOCUMENTS

2004/0127480 A1   7/2004  Gopalan et al.
2013/0303585 A1   11/2013 Dunman et al.

FOREIGN PATENT DOCUMENTS

KR   10-1147860 B1     5/2012
KR   10-2013-0082474 A 7/2013

OTHER PUBLICATIONS

Zhang et al. Inhibition of the expression of the human RNase P protein subunits Rpp21, Rpp25, Rpp29 by external guide sequences (EGSs) and siRNA. Sep. 24, 2004. Journal of Molecular Biology. vol. 342, No. 4, pp. 1077-1083.*

Childs, J.L., et al., "Inhibition of *Escherichia coli* RNase P by oligonucleotide directed misfolding of RNA", "RNA Journal", 2003, pp. 1437-1445, vol. 9.
Choi, J.H., et al., "Development of extracellular production system of recombinant proteins in recombinant *Escherichia coli*", "Microbial Cell Factories", Oct. 10, 2006, p. 86 vol. 5, No. 1.
Gossringer, M., et al., "Analysis of RNase P Protein (mpA) Expression in Bacillus subtilis Utilizing Strains with Suppressible mpA Expression", "Journal of Bacteriology", Oct. 2006, pp. 6816-6823, vol. 188, No. 19.
Gruegelsiepe, H., et al., "Antisense Inhibition of RNase P", "The Journal of Biological Chemistry", Oct. 13, 2006, pp. 30613-30620, vol. 281, No. 41.
Jung, Y.H., et al., "Alteration of RNA I Metabolism in a Temperature-Sensitive *Escherichia coli* RNPA Mutant Strain", "Biochemical and Biophysical Research Communications", Aug. 14, 1992, pp. 1463-1470, vol. 186, No. 3.
Lee, S.Y., "High cell-density culture of *Escherichia coil*", "Trends in Biotechnology", Mar. 1996, pp. 98-105, vol. 14.
Lee, S.J., et al., "Efficient High-Level Production of Spider Silk Protein by Fed-Batch Cultivation of Recombinant *Escherichia coli* and Its Purification", "Theories and Applications of Chemical Engineering", 2002, pp. 3969-3972, vol. 8, No. 2.
Lilley, M.L., et al., "The chemical origins of life and its early evolution: an introduction", "Philosophical Transactions of the Royal Society B", 2011, pp. 2853-2856, vol. 366.
Na, D., et al., "Metabolic Engineering of *Escherichia coli* Using Synthetic Small Regulatory RNAs", "Nature Biotechnology", Jan. 20, 2013, pp. 170-174, vol. 31, No. 2.
Neumann, E., et al., "Gene Transfer into Mouse Lyoma Cells by Electroporation in High Electric Fields", "The EMBO Journal", Jun. 30, 1982, pp. 841-845, vol. 1, No. 7.
Olson, P.D., et al., "Small Molecule Inhibitors of *Staphylococcus aureus* RnpA Alter Cellular mRNA Turnover, Exhibit Antimicrobial Activity, and Attenuate Pathogenesis", "PLoS Pathogens", Feb. 2011, pp. 113; e1001287, vol. 7, No. 2.
Sambrook, J., et al., "Molecular Cloning: A Laboratory Manual, 4th Edition", 2012, Page(s) Contents and Preface, Publisher: Cold Spring Harbor Laboratory Press.
Turrini, P.C.G., et al., "By Any Other Name: Heterologous Replacement of the *Escherichia coli* RNase P Protein Subunit Has In Vivo Fitness Consequences", "PLoS ONE", Mar. 2012, pp. 112; e32456, vol. 7, No. 3.
NOTE: For the non-patent literature citations that no month of publication is indicated, the year of publication is more than 1 year prior to the effective filing date of the present application.

* cited by examiner

*Primary Examiner* — Channing S Mahatan
(74) *Attorney, Agent, or Firm* — Hultquist, PLLC; Steven J. Hultquist (57) ABSTRACT

The present invention relates to a method for improving the production of a difficult-to-express recombinant protein in a recombinant microorganism, and more particularly to a method for improving the production of a difficult-to-express recombinant protein by use of a recombinant microorganism into which a gene encoding a target protein and an sRNA against a gene encoding ribonuclease P are introduced. According to the present invention, expressions of a large recombinant protein, a difficult-to-express protein and a useful protein can be dramatically increased by reducing expression of the rnpA gene.

10 Claims, 7 Drawing Sheets
(7 of 7 Drawing Sheet(s) Filed in Color)
Specification includes a Sequence Listing.

SEQUENCE LISTING

<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: sRNA of rnpA

<400> SEQUENCE: 1
gtggttaagc tcgcatttcc cagg                                        24

-continued

```
<210> SEQ ID NO 2
<211> LENGTH: 20
<212> TYPE: DNA
<213> ORGANISM: Artificial Sequence
<220> FEATURE:
<223> OTHER INFORMATION: sRNA of rnpA

<400> SEQUENCE: 2
gtggttaagc tcgcatttcc                                              20

<210> SEQ ID NO 3
<211> LENGTH: 16
<212> TYPE: DNA
<213> ORGANISM: Artificial Sequence
<220> FEATURE:
<223> OTHER INFORMATION: sRNA of rnpA

<400> SEQUENCE: 3
gtggttaagc tcgcat                                                  16

<210> SEQ ID NO 4
<211> LENGTH: 46
<212> TYPE: DNA
<213> ORGANISM: Artificial Sequence
<220> FEATURE:
<223> OTHER INFORMATION: primer

<400> SEQUENCE: 4
cctgggaaat gcgagcttaa ccactttctg ttgggccatt gcattg                 46

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
gcaaccatta tcaccgcca                                               19

<210> SEQ ID NO 6
<211> LENGTH: 1721
<212> TYPE: DNA
<213> ORGANISM: Artificial Sequence
<220> FEATURE:
<223> OTHER INFORMATION: sfcA

<400> SEQUENCE: 6
atattcaaaa aagagtgagt gacatggaac caaaaacaaa aaaacagcgt tcgctttata    60
tcccttacgc tggccctgta ctgctggaat ttccgttgtt gaataaaggc agtgccttca   120
gcatggaaga acgccgtaac ttcaacctgc tggggttact gccggaagtg gtcgaaacca   180
tcgaagaaca agcggaacga gcatggatcc agtatcaggg attcaaaacc gaaatcgaca   240
aacacatcta cctgcgtaac atccaggaca ctaacgaaac cctcttctac cgtctggtaa   300
acaatcatct tgatgagatg atgcctgtta tttataccc aaccgtcggc gcagcctgtg    360
agcgtttttc tgagatctac cgccgttcac gcggcgtgtt tatctcttac cagaaccggc   420
acaatatgga cgatattctg caaaacgtgc cgaaccataa tattaaagtg attgtggtga   480
ctgacggtga acgcattctg gggcttggtg accagggcat cggcgggatg ggcattccga   540
tcggtaaact gtcgctctat accgcctgtg gcggcatcag cccggcgtat acccttccgg   600
tggtgctgga tgtcggaacg aacaaccaac agctgcttaa cgatccgctg tatatgggct   660
```

-continued

| | |
|---|---|
| ggcgtaatcc gcgtatcact gacgacgaat actatgaatt cgttgatgaa tttatccagg | 720 |
| ctgtgaaaca acgctggcca gacgtgctgt tgcagtttga agactttgct caaaaaaatg | 780 |
| cgatgccgtt acttaaccgc tatcgcaatg aaatttgttc ttttaacgat gacattcagg | 840 |
| gcactgcggc ggtaacagtc ggcacactga tcgcagcaag ccgcgcggca ggtggtcagt | 900 |
| taagcgagaa aaaaatcgtc ttccttggcg caggttcagc gggatgcggc attgccgaaa | 960 |
| tgatcatctc ccagacccag cgcgaaggat taagcgagga agcggcgcgg cagaaagtct | 1020 |
| ttatggtcga tcgctttggc ttgctgactg acaagatgcc gaacctgctg cctttccaga | 1080 |
| ccaaactggt gcagaagcgc gaaaacctca gtgactggga taccgacagc gatgtgctgt | 1140 |
| cactgctgga tgtggtgcgc aatgtaaaac cagatattct gattggcgtc tcaggacaga | 1200 |
| ccgggctgtt tacggaagag atcatccgtg agatgcataa acactgtccg cgtccgatcg | 1260 |
| tgatgccgct gtctaacccg acgtcacgcg tggaagccac accgcaggac attatcgcct | 1320 |
| ggaccgaagg taacgcgctg gtcgccacgg gcagcccgtt taatccagtg gtatggaaag | 1380 |
| ataaaatcta ccctatcgcc cagtgtaaca acgccttat tttcccgggc atcggcctgg | 1440 |
| gtgttattgc ttccggcgcg tcacgtatca ccgatgagat gctgatgtcg gcaagtgaaa | 1500 |
| cgctggcgca gtattcacca ttggtgctga acggcgaagg tatggtactg ccggaactga | 1560 |
| aagatattca gaaagtctcc cgcgcaattg cgtttgcggt tggcaaaatg gcgcagcagc | 1620 |
| aaggcgtggc ggtgaaaacc tctgccgaag ccctgcaaca ggccattgac gataatttct | 1680 |
| ggcaagccga ataccgcgac taccgccgta cctccatcta a | 1721 |

<210> SEQ ID NO 7
<211> LENGTH: 618
<212> TYPE: DNA
<213> ORGANISM: Artificial Sequence
<220> FEATURE:
<223> OTHER INFORMATION: srtA

<400> SEQUENCE: 7

| | |
|---|---|
| atgaaaaaat ggaccaaccg cctgatgacc attgcgggcg tggtgctgat tctggtggcg | 60 |
| gcgtatctgt ttgcgaaacc gcatattgat aactatctgc atgataaaga taaagatgaa | 120 |
| aaaattgaac agtatgataa aaacgtgaaa gaacaggcga gcaaagataa aaaacagcag | 180 |
| gcgaaaccgc agattccgaa agataaaagc aaagtggcgg gctatattga aattccggat | 240 |
| gcggatatta agaaccggt gtatccgggc ccggcgaccc cggaacagct gaaccgcggc | 300 |
| gtgagctttg cggaagaaaa cgaaagcctg gatgatcaga acattagcat tgcgggccat | 360 |
| acctttattg atcgcccgaa ctatcagttt accaacctga agcggcgaa aaaaggcagc | 420 |
| atggtgtatt ttaaagtggg caacgaaacc cgcaaatata aaatgaccag cattcgcgat | 480 |
| gtgaaaccga ccgatgtggg cgtgctggat gaacagaaag gcaaagataa acagctgacc | 540 |
| ctgattacct gcgatgatta taacgaaaaa accggcgtgt gggaaaaacg caaaattttt | 600 |
| gtggcgaccg aagtgaaa | 618 |

<210> SEQ ID NO 8
<211> LENGTH: 1290
<212> TYPE: DNA
<213> ORGANISM: Artificial Sequence
<220> FEATURE:
<223> OTHER INFORMATION: Cat2

<400> SEQUENCE: 8

| | |
|---|---|
| atggagtggg aagagatata taaagagaaa ctggtaactg cagaaaaagc tgtttcaaaa | 60 |

-continued

```
atagaaaacc atagcagggt agttttttgca catgcagtag gagaacccgt agatttagta      120
aatgcactag ttaaaaataa ggataattat ataggactag aaatagttca catggtagct      180
atgggcaaag gtgaatatac aaaagagggt atgcaaagac attttagaca taatgcttta      240
tttgtaggcg gatgtactag agatgcagta aattcaggaa gagcagatta tacaccttgt      300
tttttctatg aagtgccaag tttgtttaaa gaaaaacgtt tgcctgtaga tgtagcactt      360
attcaggtaa gtgagccaga taaatatggc tactgcagtt ttggagtttc caatgactat      420
accaagccag cagcagaaag tgctaagctt gtaattgcag aagtgaataa aaacatgcca      480
agaactcttg gagattcttt tatacatgta tcagatattg attatatagt ggaagcttca      540
cacccattgt tagaattgca gcctcctaaa ttgggagatg tagaaaaagc cataggagaa      600
aactgtgcat ctttaattga agatggagct actcttcagc ttggaatagg tgctatacca      660
gatgcggtac ttttattctt aaagaacaaa aagaatttag gaatacattc tgagatgata      720
tcagatggtg tgatggaact ggtgaaggca ggggttatca ataacaagaa aaagaccctc      780
catccaggca aaatagttgt aacattttta atgggaacaa aaaaattata tgattttgta      840
aacaataatc caatggtaga aacttattct gtagattatg taaataatcc actggtaatt      900
atgaaaaatg acaatatggt ttcaataaat tcttgtgttc aagtagactt aatgggacaa      960
gtatgttctg aaagtatagg attgaaacag ataagtggag tgggaggcca ggtagatttt     1020
attagaggag ctaatctatc aaagggtgga aaggctatta tagctatacc ttccacagct     1080
ggaaaaggaa aagtttcaag aataactcca cttctagata ctggtgctgc agttacaact     1140
tctagaaatg aagtagatta tgtagttact gaatatggtg ttgctcatct taagggcaaa     1200
actttaagaa atagggcaag agctctaata aatatcgctc atccaaaatt cagagaatca     1260
ttaatgaatg aatttaaaaa gagattttag                                        1290
```

<210> SEQ ID NO 9
<211> LENGTH: 1518
<212> TYPE: DNA
<213> ORGANISM: Artificial Sequence
<220> FEATURE:
<223> OTHER INFORMATION: CYP73A5

<400> SEQUENCE: 9

```
atggacctcc tcttgctgga gaagtcttta atcgccgtct tcgtggcggt gattctcgcc       60
acggtgattt caaagctccg cggcaagaaa ttgaagctac ctccaggtcc tataccaatt      120
ccgatcttcg gaaactggct tcaagtcgga gatgatctca accaccgtaa tctcgtcgat      180
tacgctaaga aattcggcga tctcttcctc ctccgtatgg gtcagcgaaa cctagtcgtc      240
gtctcctcac cggatctaac aaaggaagtg ctcctcactc aaggcgttga gtttggatcc      300
agaacgagaa acgtcgtgtt cgacattttc accgggaaag gtcaagatat ggtgttcact      360
gtttacggcg agcattggag gaagatgaga agaatcatga cggttccttt cttcaccaac      420
aaagttgttc aacagaatcg tgaaggttgg gagtttgaag cagctagtgt tgttgaagat      480
gttaaggaga atccagattc tgctacgaaa ggaatcgtgt tgaggaaacg tttgcaattg      540
atgatgtata caaatatgtt ccgtatcatg ttcgataaga gatttgagag tgaggatgat      600 cctctttttcc ttaggcttaa ggctttgaat ggtgagagaa gtcgattagc tcagagcttt      660
gagtataact atgagatttt cattcctatc cttagaccat tcctcagagg ctatttgaag      720
atttgtcaag atgtgaaaga tcgaagaatc gctcttttca gaagtacttt tgttgatgag      780
```

| | |
|---|---|
| aggaagcaaa ttgcgagttc taagcctaca ggtagtgaag gattgaaatg tgccattgat | 840 |
| cacatccttg aagctgagca gaagggagaa atcaacgagg acaatgttct ttacatcgtc | 900 |
| gagaacatca atgtcgccgc gattgagaca acattgtggt ctatcgagtg gggaattgca | 960 |
| gagctagtga accatcctga aatccagagt aagctaagga acgaactcga cacagttctt | 1020 |
| ggaccgggtg tgcaagtcac cgagcctgat cttcacaaac ttccatacct tcaagctgtg | 1080 |
| gttaaggaga ctcttcgtct gagaatggcg attcctctcc tcgtgcctca catgaacctc | 1140 |
| catgatgcga agctcgctgg ctacgatatc ccagcagaaa gcaaaatcct tgttaatgct | 1200 |
| tggtggctag caaacaaccc caacagctgg aagaagcctg aagagtttag accagagagg | 1260 |
| ttctttgaag aagaatcgca cgtggaagct aacggtaatg acttcaggta tgtgccattt | 1320 |
| ggtgttggac gtcgaagctg tcccgggatt atattggcat tgcctatttt ggggatcacc | 1380 |
| attggtagga tggtccagaa cttcgagctt cttcctcctc caggacagtc taaagtggat | 1440 |
| actagtgaga aggtggaca attcagcttg cacatcctta accactccat aatcgttatg | 1500 |
| aaaccaagga actgttaa | 1518 |

<210> SEQ ID NO 10
<211> LENGTH: 1527
<212> TYPE: DNA
<213> ORGANISM: Artificial Sequence
<220> FEATURE:
<223> OTHER INFORMATION: CYP98A3

<400> SEQUENCE: 10

| | |
|---|---|
| atgtcgtggt ttctaatagc ggtgcgaca atcgccgccg tcgtatccta caagctaatc | 60 |
| caacggctaa gatacaagtt cccaccaggc ccaagcccca agccgatcgt cggtaacctc | 120 |
| tacgacataa aaccggtccg gttcagatgt tactacgagt gggctcaatc ttatggacca | 180 |
| atcatatcgg tctggatcgg ttcaattcta aacgtggtcg tatctagcgc cgagctagca | 240 |
| aaagaagttc tgaaagaaca cgaccagaaa ctcgccgacc ggcaccggaa cagatcgacg | 300 |
| gaagcattta gccgcaacgg tcaggatctt atatgggccg attatgggcc tcattacgtg | 360 |
| aaggtgagaa agtttgcac gcttgagctc ttcacaccga aacgactcga gtctctcaga | 420 |
| cctatccgtg aagatgaagt caccgccatg gttgaatccg tcttcagaga ctgtaacctt | 480 |
| cctgaaaaca gagcaaaagg tttacaactg aggaagtact taggagcggt tgcgttcaac | 540 |
| aacataacgc ggctagcctt tgggaagcgt tttatgaacg ctgaaggtgt tgtggacgag | 600 |
| caagggcttg agttcaaggc catagtatcc aacggtctga agctaggtgc ttcactgtca | 660 |
| atagctgaac acatcccgtg gctcaggtgg atgtttccgg ctgatgagaa ggcgtttgct | 720 |
| gagcacgggg ctcgtcgtga ccgcctcact cgagctatca tggaggagca tacttttggcc | 780 |
| cgtcaaaagt ctagtggagc gaaacagcat tcgttgatg cgttgctaac gttgaaggat | 840 |
| cagtatgatc ttagtgagga tactatcatt ggtcttctat gggatatgat cacggcaggg | 900 |
| atggacacga cagcgataac agcggaatgg gcgatggcgg aaatgatcaa gaatccaaga | 960 |
| gtgcaacaaa agtgcaaga agagttcgac agagtggttg gacttgaccg gatcttaacc | 1020 |
| gaggcagatt tctcccgctt accttacttg caatgcgtgg tgaaagagtc attcaggctg | 1080 |
| catcctccaa cgcctctaat gctacctcac cgaagcaacg cagatgtcaa gatcggaggc | 1140 |
| tatgatattc ccaaaggatc aaacgttcat gtgaatgtgt gggctgtggc tagagacccg | 1200 |
| gctgtatgga aaaatccatt tgagtttaga ccagagagat tcttggaaga agatgttgac | 1260 |
| atgaagggtc atgattttag gctgcttccg tttggagctg gaagacgggt ttgtcccggt | 1320 |

```
gcacaacttg gtatcaattt ggtaacttcg atgatgagtc atttgcttca ccattttgtt    1380
tggacacctc ctcaagggac taaaccggag gagattgaca tgtctgaaaa ccctggactc    1440
gttacttaca tgcgtacccc tgtgcaagcg gttgcaacgc ctcggttgcc ttcggatctg    1500
tacaaacgcg tgccttacga tatgtaa                                       1527

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
ccatggatat tcaaaaaaga gtgagt                                        26

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
tctagattag atggaggtac ggcggta                                       27

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
gaattcatgg agtgggaaga gatatata                                      28

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
ggtaccctaa aatctctttt taaattcatt                                    30

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
gcgaagctta cagttccttg gtttcataa                                     29

<210> SEQ ID NO 16
<211> LENGTH: 28
<212> TYPE: DNA
<213> ORGANISM: Artificial Sequence
<220> FEATURE:
<223> OTHER INFORMATION: primer

<400> SEQUENCE: 16
```

-continued

```
gtacatatga tggacctcct cttgctgg                                              28

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
ggatccatgt cgtggtttct aatagc                                                26

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
gaattcttac atatcgtaag gcacgc                                                26

<210> SEQ ID NO 19
<211> LENGTH: 34
<212> TYPE: PRT
<213> ORGANISM: Artificial Sequence
<220> FEATURE:
<223> OTHER INFORMATION: Silk protein amino acid repeat sequence

<400> SEQUENCE: 19

Ser Gly Arg Gly Gly Leu Gly Gly Thr Gly Ala Gly Met Ala Ala Ala
1               5                  10                  15

Ala Ala Met Gly Gly Ala Gly Gln Gly Gly Tyr Gly Gly Leu Gly Ser
            20                  25                  30

Gln Gly
```

METHOD FOR PREPARING RECOMBINANT PROTEINS THROUGH REDUCTION OF RNPA GENE EXPRESSION

CROSS-REFERENCE TO RELATED APPLICATIONS

This application is a U.S. national phase under the provisions of 35 U.S.C. § 371 of International Patent Application No. PCT/KR2015/013419 filed Dec. 9, 2015, which in turn claims priority of Korean Patent Application No. 10-2014-0175780 filed Dec. 9, 2014 and Korean Patent Application No. 10-2015-0174828 filed Dec. 9, 2015. The disclosures of such international patent application and Korean priority patent applications are hereby incorporated herein by reference in their respective entireties, for all purposes.

TECHNICAL FIELD

The present invention relates to a method for improving the production of a recombinant protein in a recombinant microorganism, and more particularly to a method for improving the production of a recombinant protein by use of a recombinant microorganism into which a gene encoding a target protein and an sRNA against a gene encoding ribonuclease P are introduced.

BACKGROUND ART

The development of genetic manipulation technology has led to many studies focused on producing large amounts of useful proteins using bacterial and a variety of animals and plants. Host cells for producing large amounts of useful proteins are present, including bacteria such as *E. coli*, and yeasts such as *P. pastoris*. Of these host cells, *E. coli* has been most widely used, and studies thereon have been most frequently conducted (Choi et al., Chem. Eng. Sci., 66: 876, 2006; Lee, Trends Biotechnol., 14:98, 1996).

However, if the useful protein to be produced is larger in size than a naturally occurring protein or is difficult to express, many problems may arise. If the size of a protein is large, translation of the protein may be difficult due to lack of messenger RNA (mRNA), and thus expression of the desired full-length protein may be difficult. In addition, a recombinant protein that is not naturally present in *E. coli* may be difficult to express, due to proteolysis and RNase-induced degradation of mRNA (GoBringer et al., J Bacteriol., 188: 6816, 2006; Olson et al., PLoS Pathog., 7(2): e1001287, 2011; Jung et al., Biochem Biophys Res Commun., 186(3):1463, 1992; Altman et al., Phil Trans R Soc., 366, 2011; Turrini et al., PLos One., 7(3): e32456, 2012).

Accordingly, the present inventors have made extensive efforts to develop a protein expression system for increasing the production of a difficult-to-express foreign protein, and as a result, have found that, when expression of the rnpA gene (which is a component of ribonuclease P) in a process of expressing the foreign protein by introducing a gene encoding the foreign protein is reduced, expression of the difficult-to-express foreign protein increases, thereby completing the present invention.

DISCLOSURE OF INVENTION

Technical Problem

It is a main object of the present invention to provide a recombinant microorganism into which a gene encoding a target protein and an sRNA against a gene encoding Ribonuclease P are introduced to increase the production of a difficult-to-express foreign protein.

Another object of the present invention is to provide a method for producing a target protein by culturing the above-described recombinant microorganism.

Technical Solution

To achieve the above objects, the present invention provides a recombinant vector for expressing a target protein, which comprises a gene encoding the target protein and an sRNA against a gene encoding ribonuclease P, and a recombinant microorganism into which the recombinant vector is introduced.

The present invention also provides a recombinant microorganism into which a gene encoding a target protein and an sRNA against a gene encoding ribonuclease P are introduced.

The present invention also provides a method for producing a target protein, the method comprising the steps of: (a) producing the target protein by culturing the above-described recombinant microorganism and inducing expression of the target protein in the recombinant microorganism; and (b) recovering the produced target protein.

The present invention also provides a method for producing a target protein, comprising the steps of: expressing and producing the target protein by culturing a recombinant microorganism into which a gene encoding the target protein is introduced; and recovering the produced target protein, wherein expression of ribonuclease P is reduced to increase expression of the target protein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 shows the results of electrophoresis performed using a system for reducing expression of the rnpA gene according to the present invention in order to confirm increased expressions of difficult-to-express proteins other than the silk protein. Specifically, electrophoresis image (a) shows the results of analyzing the expression level of malic enzyme (SfcA) by SDS-PAGE. (lane 1: a marker showing protein standard molecular weight; lane 2: the result of inducing protein expression in non-transformed BL21 (DE3); lanes 3 and 4: the results of inducing protein expression in a strain transformed with SfcA at an $OD_{600}$ of 0.4; and lanes 5 and 6: the results of inducing protein expression in a strain transformed with SfcA and rnpA(sRNA) at an $OD_{600}$ of 0.4.) Electrophoresis image (b) shows the results of analyzing the expression level of Cat2 by SDS-PAGE. (lane 1: a marker showing protein standard molecular weight; lanes 2 and 3: the results of inducing protein expression in a strain transformed with Cat2 at an $OD_{600}$ of 0.4; and lanes 4 and 5: the results of inducing protein expression in a strain transformed with Cat2-rnpA(sRNA) at an $OD_{600}$ of 0.4.) Electrophoresis image (c) shows the results of analyzing the expression level of SrtA by SDS-PAGE. (lane 1: a marker showing protein standard molecular weight; lanes 2 and 3: the results of inducing protein expression in a strain transformed with SrtA at an $OD_{600}$ of 0.4; and lanes 4 and 5: the results of inducing protein expression in a strain transformed with srtA-rnpA(sRNA) at an $OD_{600}$ of 0.4.) Electrophoresis image (d) shows the results of analyzing the expression level of CYP73A5 by SDS-PAGE. (lane 1: a marker showing protein standard molecular weight; lanes 2 and 3: the results of inducing protein expression in a strain transformed with CYP73A5 at an $OD_{600}$ of 0.4; and lanes 4 and 5: the results of inducing protein expression in a strain transformed with CYP73A5-rnpA(sRNA) at an $OD_{600}$ of 0.4.) Electrophoresis image (e) shows the results of analyzing the expression level of CYP98A3 by SDS-PAGE. (lane 1: a marker showing protein standard molecular weight; lanes 2 and 3: the results of inducing protein expression in a strain transformed with CYP98A3 at an $OD_{600}$ of 0.4; and lanes 4 and 5: the results of inducing protein expression in a strain transformed with CYP98A3-rnpA(sRNA) at an $OD_{600}$ of 0.4.)

BEST MODE FOR CARRYING OUT THE INVENTION

The present inventors have developed a method for improving expression of a difficult-to-express recombinant protein, which was not easily produced in the prior art, in a recombinant microorganism by reducing expression of ribonuclease P to increase the mRNA level of a useful protein in cells.

In the present invention, expression of the rnpA gene that is a component of ribonuclease P was reduced using a sRNA system comprising sRNA, and as a result, it was shown that expression of a high-molecular-weight silk protein that is a difficult-to-express protein was increased dramatically.

As used herein, the term "difficult-to-express protein" refers to a protein having a molecular weight of 50 kDa or more.

Therefore, in one aspect, the present invention is directed to a recombinant vector for expressing a target protein, which comprises a gene encoding the target protein and an sRNA against a gene encoding ribonuclease P, and to a recombinant microorganism transformed with the recombinant vector.

In the present invention, the target protein may be a protein selected from among difficult-to-express proteins silk proteins, antibodies, enzymes, cytochromes, and sortase A, but is not limited thereto.

In the present invention, the sRNA may be an sRNA against an rnpA gene, and may have a nucleotide sequence set forth in any one of SEQ ID NOs: 1 to 3, but is not limited thereto as long as it reduces the expression of an rnpA gene.

In the present invention, examples of microorganisms for production of proteins that can be used may include *Escherichia*, *Pseudomonas*, *Saccharomyces*, and the like, and may be preferably an *Escherichia* microorganism, most preferably *E. coli*. In particular, it is advantageous that *E. coli* can be easily industrialized since genetic information and culture conditions that are widely used industrially are very well known.

In an example of the present invention, a recombinant *E. coli* strain was constructed by transformation with a gene encoding a silk protein resulting from modification of a dragline silk protein obtained from *Nephila clavipes*, a nucleotide sequence encoding glycine tRNA, and an sRNA for reducing expression of the RnpA that is a component of ribonuclease P. The constructed recombinant *E. coli* strain was cultured. As a result, it could be seen that the protein of the silk protein increased 3-fold or more. In addition, it was shown that expression of a silk protein consisting of 16, 32, 48, 64, 80, 96, 112 and 128 repeats of a specific amino acid sequence (SGRGGLGGTGAGMAAAAAMGGAGQG-GYGGLGSQG) (SEQ ID NO: 19) was dramatically increased by reducing expression of the rnpA gene that is a component of ribonuclease P. Furthermore, it was shown that expressions of eGFP, SfcA and a full-length IgG antibody were also dramatically increased by reducing expression of the rnpA gene that is a component of ribonuclease P.

In view of the results indicating that the production of a long recombinant protein or a difficult-to-express protein is increased by reducing expression of the rnpA gene that is a component of ribonuclease P, it will be obvious to those skilled in the art that the degradation of messenger RNA (mRNA) has a great influence on protein expression and that overexpression of a target protein can be effectively achieved by reducing expression of a gene associated with messenger RNA (mRNA) degradation.

In another example of the present invention, the expressions of a malic enzyme-encoding gene (sfcA), a sortase A-encoding gene (srtA), a 4-hydroxybutyrate coenzyme A transferase-encoding gene (Cat2) and the cytochrome P450 gene (CYP73A5; cinnamate 4-hydrosylase and CYP98A3) were examined using the system for reducing expression of the rnpA gene according to the present invention. As a result, it was shown that a strain expressing an sRNA against the rnpA gene together with the gene encoding each of the proteins showed a higher protein expression level compared to a strain expressing no sRNA (FIG. 8; see electrophoresis images (a) through (e)).

In another aspect, the present invention is directed to a recombinant microorganism into which a gene encoding a target protein and an sRNA against a gene encoding ribonuclease P are introduced.

In the present invention, the gene encoding the target protein and the sRNA against the gene encoding ribonuclease P may be present in the respective vectors or may be incorporated into the microbial chromosome.

In still another aspect, the present invention is directed to a method for producing a difficult-to-express target protein, the method comprising the steps of: (a) producing the target protein by culturing the recombinant microorganism and inducing expression of the target protein in the recombinant microorganism; and (b) recovering the produced target protein.

In an example of the present invention, a recombinant *E. coli* strain was constructed by transformation with a gene encoding a silk protein, a nucleotide sequence encoding glycine tRNA, and an sRNA for reducing expression of the rnpA gene that is a component of ribonuclease P. The constructed recombinant *E. coli* strain was cultured. As a result, it could be seen that the protein of the silk protein increased 3-fold or more.

In another example of the present invention, it was shown that, when a gene encoding eGFP protein, a gene encoding sfcA protein and a gene encoding a full-length IgG antibody protein were co-expressed with an sRNA against the rnpA gene, expressions of the proteins increased.

In the present invention, preferably, the target protein may be a large protein having a molecular weight of 50 kDa or more as a difficult-to-express protein. For example, the target protein may be a protein selected from a group consisting of silk proteins, antibodies, enzymes, cytochromes, and sortase A, but is not limited thereto.

In still another aspect, the present invention is directed to a method for producing a target protein, comprising the steps of: expressing and producing the target protein by culturing a recombinant microorganism into which a gene encoding the target protein is introduced; and recovering the produced target protein, wherein expression of ribonuclease P in the recombinant microorganism is reduced to increase expression of the target protein.

In the present invention, the target protein may be a difficult-to-express protein or a protein having a molecular weight of 50 kDa or more, and a substance of inhibiting the expression of ribonuclease P may be added.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

The definition of main terms used in the detailed description of the invention is as follows.

As used herein, the term "sRNA (small RNA)" refers to a short-length RNA, which is usually 200 or less nucleotides in length, which is not translated into protein and effectively inhibits the translation of a specific mRNA by complementary binding.

As used herein, the term "ribosome binding site" refers to a site where ribosome binds to mRNA for the transcription of the mRNA.

As used herein, the term "gene" is intended to have the broadest meaning, and the gene can encode a structural protein or a regulatory protein. Herein, the regulatory protein includes a transcriptional factor, a heat shock protein, or a protein that is involved in DNA/RNA replication, transcription and/or translation. Also, the target gene whose expression is to be inhibited may be present as an extrachromosomal element.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably, as the plasmid is the most commonly used form of vector. For the purpose of the present invention, the plasmid vector is preferably used. A typical plasmid vector which can be used for this purpose contains: (a) a replication origin by which replication occurs efficiently such that several hundred plasmid vectors per host cell are created; (b) an antibiotic-resistant gene by which host cells transformed with the plasmid vector can be selected; and (c) restriction enzyme cutting sites into which foreign DNA fragments can be inserted. Even if suitable restriction enzyme cutting sites are not present in the vector, the use of a conventional synthetic oligonucleotide adaptor or linker enables the easy ligation between the vector and the foreign DNA fragments. After ligation, the vector should be transformed into suitable host cells. The transformation can be easily achieved by the calcium chloride method or electroporation (Neumann, et al., *EMBO J.*, 1:841, 1982). A publicly known expression vector in the art may be used as a vector for expressing sRNA according to the present invention.

A nucleic acid sequence is operably linked when it is placed into arranged in a functional relationship with another nucleic acid sequence. The nucleotide sequence may be a gene and a control sequence(s) linked to be capable of expressing the gene when a suitable molecule binds to a control sequence(s) (e.g., transcription-activating protein). For example, DNA for a pre-sequence or a secretory leader is operably linked to a DNA encoding a polypeptide when expressed as a pre-protein participating in secretion of the polypeptide; a promoter or an enhancer is operably linked to a coding sequence when affecting the transcription of the sequence; or a ribosome binding site is operably linked to a coding sequence when affecting the transcription of the sequence, or to a coding sequence when arranged to facilitate translation. Generally, the term "operably linked" means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site.

However, when this site does not exist, a synthetic oligonucleotide adaptor or a linker is used according to a conventional method.

In addition, the present invention is directed to a recombinant microorganism into which an expression vector comprising a nucleic acid encoding the sRNA is introduced. As used herein, the term "transformation" means that DNA can be replicated as a factor outside of chromosome or by means of completion of the entire chromosome by introducing DNA as a host.

Of course, it should be understood that all vectors and expression control sequences do not equally function to express DNA sequences according to the present invention. Similarly, all hosts do not equally function with respect to the same expression system. However, one skilled in the art may appropriately select from a group consisting of various vectors, expression control sequences, and hosts without either departing from the scope of the present invention or bearing excessive experimental burden. For example, a vector must be selected considering a host, because the vector must be replicated in the host. Specifically, the copy number of the vector, the ability of regulating the copy number and the expression of other protein encoded by the corresponding vector (e.g., the expression of an antibiotic marker) should also be considered.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Construction of Recombinant Plasmid pTetlgy2glyAN-rnpA(sRNA)

All procedures for gene manipulation followed standardized methods (Sambrook et al., Molecular cloning: a laboratory manual, 2nd Ed., Cold Spring Harbor Laboratory Press, Cold Spring Harbor, N.Y., 1989).

To introduce an sRNA system into a pTetlgy2glyAN vector (Korean Patent No. 1147860), genetic manipulation was performed, and to obtain a ribosome binding site that is involved in translation of the rnpA gene, inverse-PCR was performed using primers of SEQ ID NOs: 4 and 5, thereby obtaining an rnpA sRNA (SEQ ID NO: 1).

```
SEQ ID NO: 4:
5'-cctgggaaatgcgagcttaaccactttctgttgggccattgcattg-
3'

SEQ ID NO: 5:
5'-GCAACCATTATCACCGCCA-3
```

The PCR reaction was performed using Pfu polymerase (SolGent, Korea) under the following conditions: pre-denaturation at 95° C. for 5 min, and then 28 cycles, each consisting of denaturation at 95° C. for 30 sec, annealing at 57° C. for 180 sec, and extension at 72° C. for 60 sec, followed by final extension at 72° C. for 5 min.

The PCR product was electrophoresed on agarose gel to obtain a purified 5000-bp PCR product. The purified PCR product was incubated with the restriction enzyme DpnI (New England Biolabs, USA) for 1 hour, and then ligated with a pTetlgy2glyAN by T4 DNA ligase (Roche, Germany), and the resulting vector was transformed into E. coli dH5α (FhuA2 lac(del)U169 phoA glnV44 Φ80' lacZ(del) M15 gyrA96 recA1 relA1 endA1 thi-1 hsdR17, Invitrogen).

Figure 1:
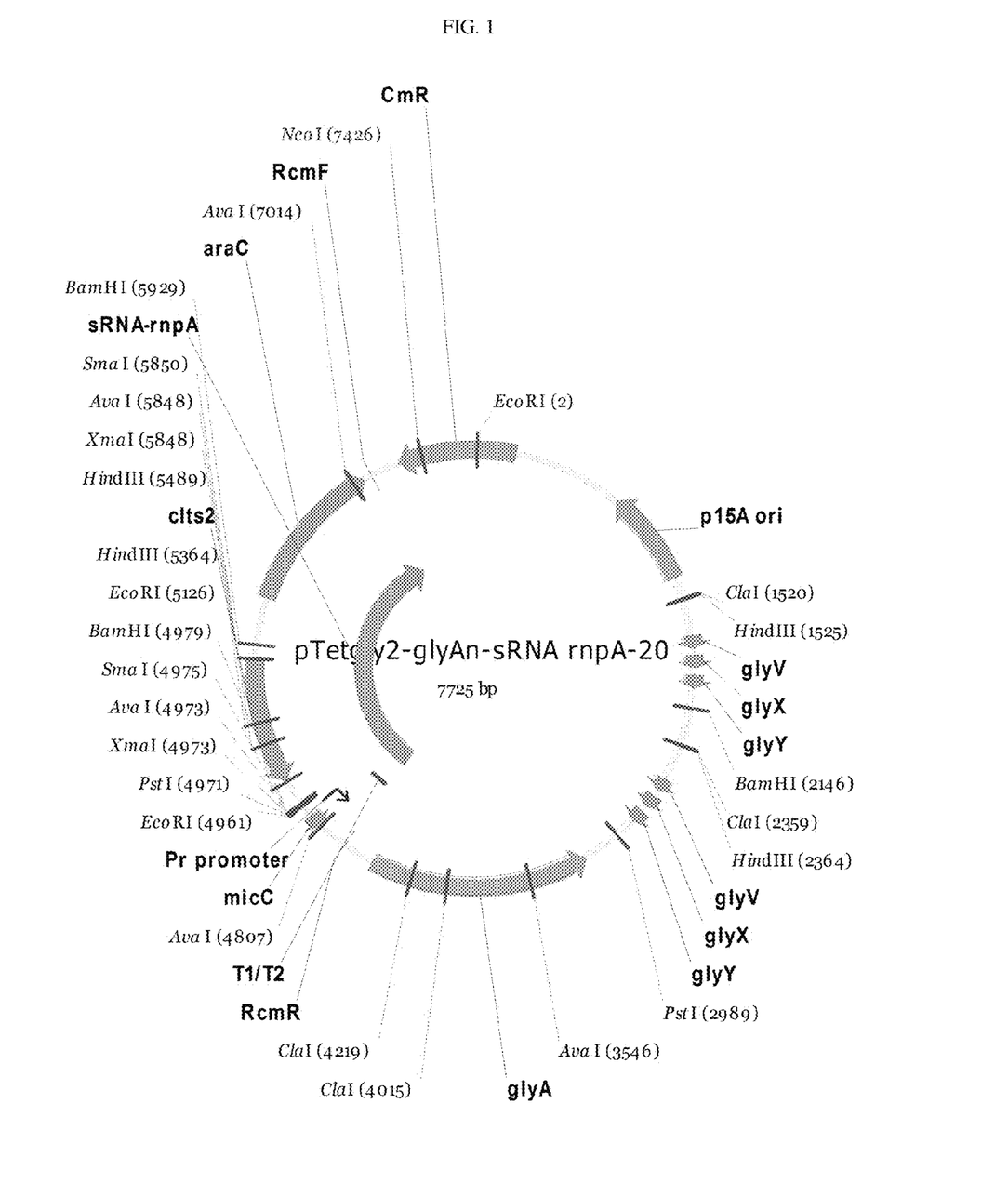
FIG. 1 is a gene map of the plasmid pTetly2glyAN-rnpA (sRNA).
Figure 2:
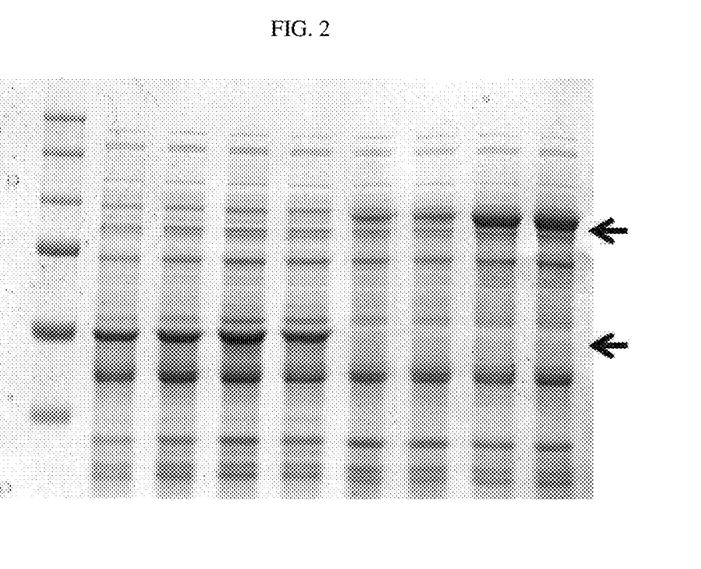
FIG. 2 shows the results of analyzing expression levels of a silk protein consisting of 16 repeats and a silk protein consisting of 32 repeats by SDS-PAGE. (lane 1: a marker showing protein standard molecular weight; lanes 2 and 3: the results of inducing protein expression in a stain transformed with the plasmid pSH16 at an $OD_{600}$ of 0.4; lanes 4 and 5: the results of inducing protein expression in a strain transformed with the plasmid pSH16 and pACYC184-rnpA (sRNA) at an $OD_{600}$ of 0.4; lanes 6 and 7: the results of inducing protein expression in a strain transformed with the plasmid pSH32 at an $OD_{600}$ of 0.4; and lanes 8 and 9: the results of inducing protein expression in a strain transformed with the plasmid pSH32 and pACYC184-rnpA(sRNA) at an $OD_{600}$ of 0.4.)
Figure 3:
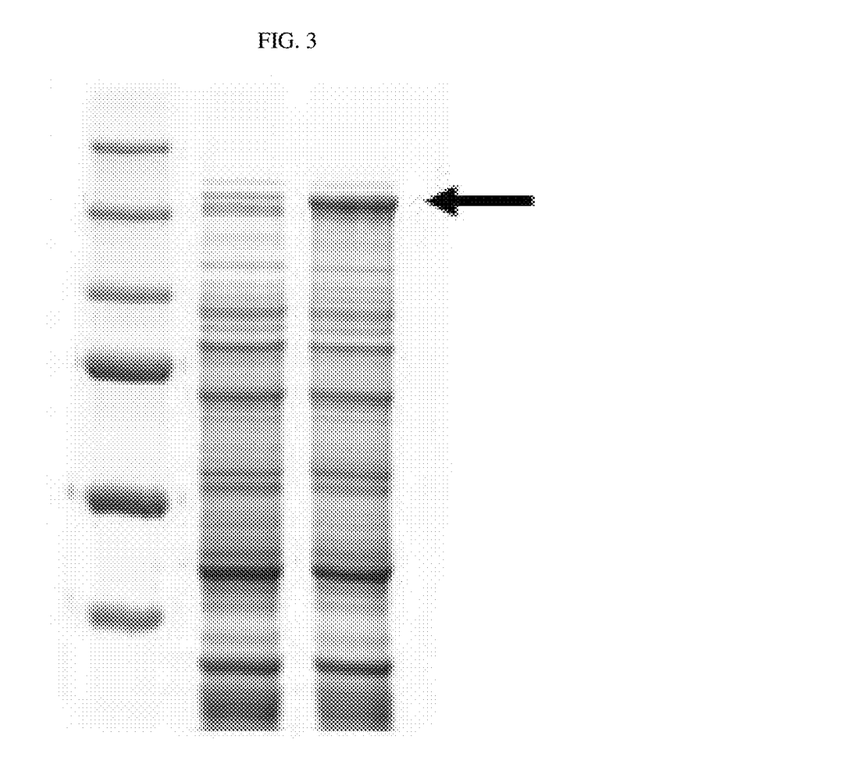
FIG. 3 shows the results of analyzing expression levels of a silk protein consisting of 64 repeats by SDS-PAGE. (lane 1: a marker showing protein standard molecular weight; lane 2: the result of inducing protein expression in a strain transformed with pSH64 at an $OD_{600}$ of 0.4; and lane 3: the result of inducing protein expression in a strain transformed with the plasmid pSH64 and pACYC184-rnpA(sRNA) at an $OD_{600}$ of 0.4.)

The transformed strain was selected on an LB agar solid medium (tryptone 10 g/L, yeast extract 5 g/L, NaCl 5 g/L, and agar 15 g/L) containing 34 mg/L of chloramphenicol, thereby obtaining the recombinant plasmid pTetgly2glyAN-rnpA(sRNA) (FIG. 1). The constructed recombinant plasmid was confirmed by cleaving with restriction enzymes and DNA sequencing.

Example 2: Construction of Recombinant Plasmids Containing the Gene Encoding High-Molecular-Weight Silk Protein In order to construct a recombinant plasmid containing 32 repeats of a gene that encodes a silk protein resulting from modification of a Nephila clavipes derived dragline silk protein that is a difficult-to-express protein having a large size, the plasmid pSH16a (Lee et al., Theories and Applications of Chem. Eng., 8:3969, 2002) consisting of 16 repeats of the gene encoding the silk protein was digested with the restriction enzyme SpeI and NheI to obtain a 1.7-kb fragment. The fragment was ligated with the plasmid pSH16a digested with the restriction enzyme SpeI, thereby obtaining the recombinant plasmid pSH32. The direction of the ligated insert was determined by digestion with the restriction enzyme SpeI and NheI (New England Biolabs, USA).

Similarly, the plasmid pSH16a was digested with the restriction enzyme SpeI and NheI to obtain a 1.7-kb fragment which was then ligated with the plasmid pSH32 digested with the restriction enzyme SpeI, thereby constructing the recombinant plasmid pSH48. The recombinant plasmid pSH32 was digested with the restriction enzyme SpeI and NheI to obtain a 3.4-kb fragment which was then ligated with the plasmid pSH64 digested with the restriction enzyme SpeI, thereby constructing the recombinant plasmid pSH64. The plasmid pSH48 was digested with the restriction enzyme SpeI and NheI to obtain a 5.1-kb fragment which was then ligated with the plasmid pSH32 digested with the restriction enzyme SpeI, thereby constructing the recombinant plasmid pSH80. The plasmid pSH16 was digested with the restriction enzyme SpeI and NheI to obtain a 1.74-kb fragment which was then ligated with the plasmid pSH80 digested with the restriction enzyme SpeI, thereby constructing the recombinant plasmid pSH96. The plasmid pSH32 was digested with the restriction enzyme SpeI and NheI to obtain a 3.4-kb fragment which was then ligated with the plasmid pSH80 digested with the restriction enzyme SpeI, thereby constructing the recombinant plasmid pSH112. The plasmid pSH64 was digested with the restriction enzyme SpeI and NheI to obtain a 7.8-kb fragment which was then ligated with the plasmid pSH64 digested with the restriction enzyme SpeI, thereby constructing the recombinant plasmid pSH128. The direction of each ligated insert was determined by digestion with the restriction enzyme SpeI and NheI.

Example 3: Examination of the Increase in Silk Protein Expression Caused by the Reduction in Expression of rnpA Gene by sRNA System In order to examine the effect of co-overexpressing the glycine tRNA gene and reducing the expression of the ribonuclease P (rnpA) gene by use of the sRNA system in silk protein production, E. coli BL21 (DE3) (F-ompT hsdSB (rB-mB-) gal dcm (DE3) a prophage carrying the T7 RNA polymerase gene) (New England Biolabs, USA) was transformed with the plasmid pTetgly2glyAN-rnpA(sRNA) obtained in Example 1 and each of the plasmid pSH16, pSH32, pSH48, pSH64, pSH80, pSH96 and pSH112 containing 16, 32, 48, 64, 80, 96 and 112 repeats of the silk protein-encoding gene, respectively.

As a control, *E. coli* BL21 (DE3), transformed with the plasmid pACYC184 and each of pSH16, pSH32, pSH64, pSH96 and pSH128, was used. Each of the transformed strains was seeded into 10 ml of an LB liquid medium (tryptone 10 g/L, yeast extract 5 g/L, and NaCl 5 g/L) (containing 34 mg/L of chloramphenicol, 25 mg/L of kanamycin and 1% arabinose) and shake-cultured at 25° C. and 220 rpm. Next, each of the strains was shake-cultured under the above-described medium conditions at 37° C. and 220 rpm. When the culture reached an $OD_{600}$ of 0.4, 1 mM IPTG was added to the medium to induce expression of the silk protein gene. At 4 hours after induction of the expression, the culture was sampled and centrifuged at 4° C. and 10,000 g for 10 minutes, and the obtained cell pellets were dissolved in TE buffer and 5× Laemmli sample buffer. The same amount (0.024 mg) of the sample was separated using 10% SDS-PAGE gel, after which it was stained with Coomassie brilliant blue R250 (Bio-Rad, USA) solution and quantified using the GS-710 Calibrated Imaging Densitometer (Bio-Rad, USA) (see FIGS. 2, 3, 4A, and 4B).

Figure 4A:
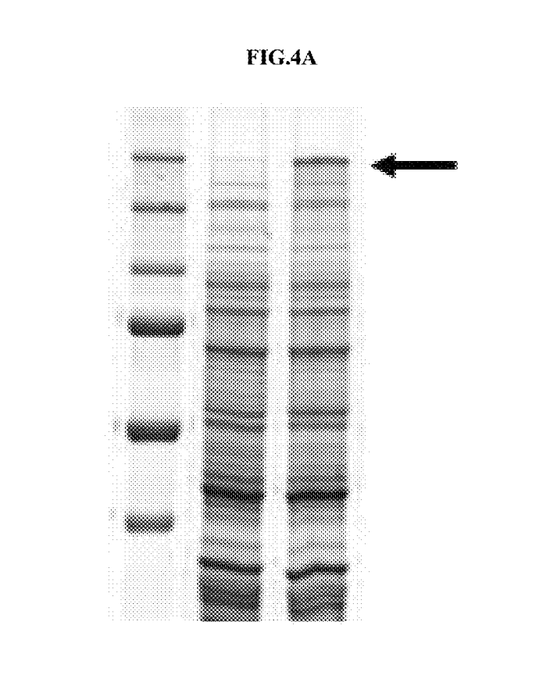
FIG. 4A shows the results of analyzing expression levels of a silk protein consisting of 96 repeats by SDS-PAGE. (lane 1: a marker showing protein standard molecular weight; lane 2: the result of inducing protein expression in a strain transformed with pSH96 at an $OD_{600}$ of 0.4; and lane 3: the result of inducing protein expression in a strain transformed with the plasmid pSH96 and pACYC184-rnpA (sRNA) at an $OD_{600}$ of 0.4.)
Figure 4B:
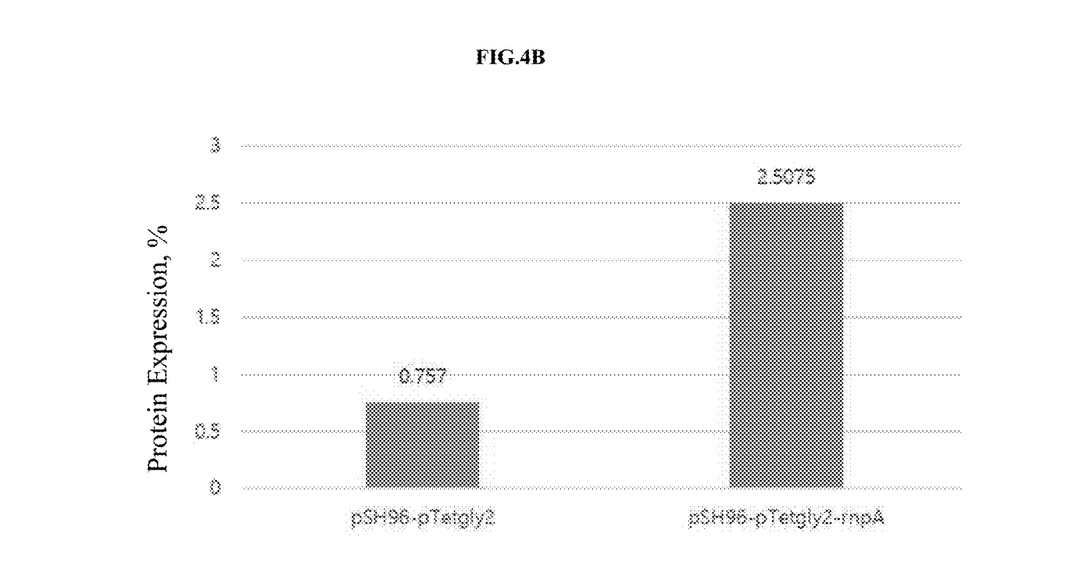
FIG. 4B shows the results obtained by inducing protein expression in strains transformed with the plasmid pSH96 and the plasmid pSH96 plus pTetgly2glyAN-rnpA(sRNA), respectively, at an $OD_{600}$ of 0.4, analyzing protein expression levels by SDS-PAGE, quantifying the protein expression levels using a densitometer, and then averaging the protein expression levels.
Figure 5:
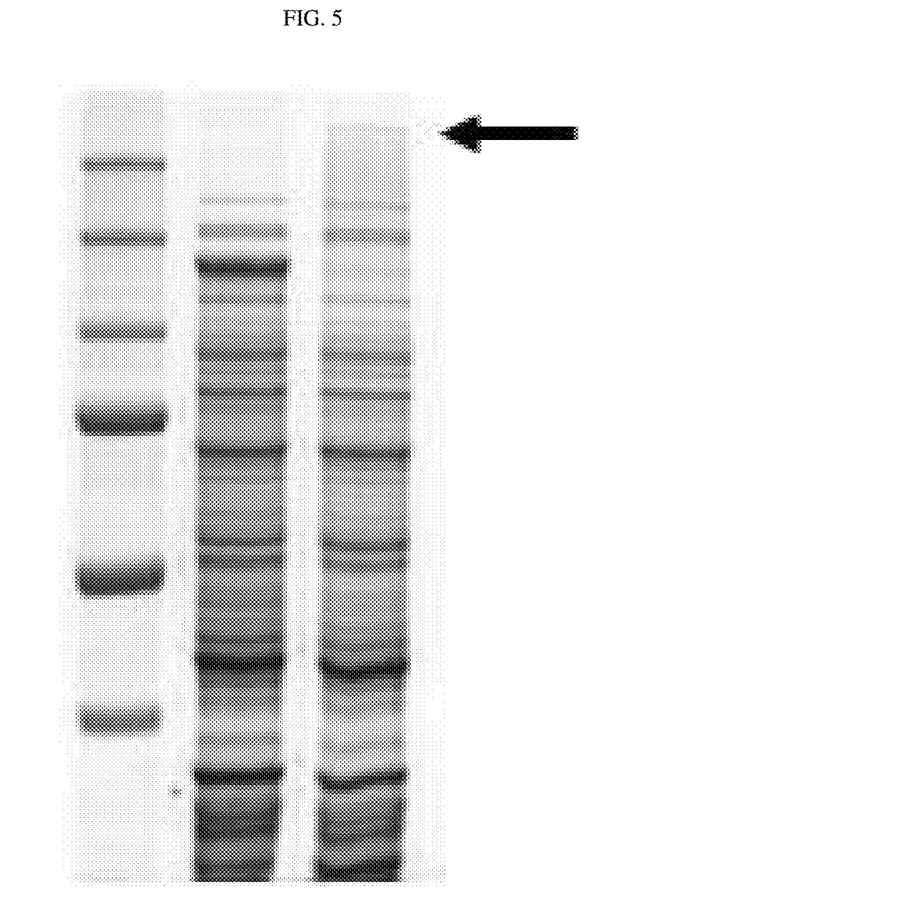
FIG. 5 shows the result of analyzing expression levels of a silk protein consisting of 128 repeats by SDS-PAGE. (lane 1: a marker showing protein standard molecular weight; lane 2: the result of inducing protein expression in a strain transformed with pSH128 at an $OD_{600}$ of 0.4; and lane 3: the result of inducing protein expression in a strain transformed with pSH128 and pACYC184-rnpA(sRNA) at an $OD_{600}$ of 0.4.)

Furthermore, expression of the strain transformed with the plasmid pSH96 and pTetgly2glyAN-rnpA(sRNA) was induced at an $OD_{600}$ 0.4, after which protein expression was analyzed by SDS-PAGE, quantified using a densitometer and averaged. The results are shown in FIG. 4B. In addition, the results of expression performed using the plasmid pSH128 are shown in FIG. 5.

As a result, it could be seen that, due to the reduction in expression of ribonuclease P (RnpA), expression of the silk protein consisting of 16 repeats was increased by about 150% compared to the control, and expression of the silk protein consisting of 32 repeats was increased by about 300% compared to the control. Furthermore, expression of the silk protein consisting of 48 repeats was increased by about 300%, and expression of the silk protein consisting of 64 repeats was increased by about 300%. In addition, expression of the silk protein consisting of 80 repeats was increased by about 300%, expression of the silk protein consisting of 112 repeats was increased by about 200%, and expression of the silk protein consisting of 128 repeats was increased by about 150%.

Example 4: Examination of the Increase in mRNA Level Caused by the Reduction in Expression of rnpA Gene by sRNA System In this Example, in order to prevent the degradation of messenger RNA in the production of recombinant, difficult-to-express and useful proteins, expression of the rnpA gene that is a component of ribonuclease P was reduced by introduction of the sRNA system. In addition, whether the level of intracellular mRNA would be increased by the reduction in expression of the rnpA gene was examined.

Specifically, *E. coli* BL21 (DE3) (F-ompT hsdSB(rB- mB-) gal dcm (DE3) a prophage carrying the T7 RNA polymerase gene) (New England Biolabs, USA) was transformed with the plasmid pTetgly2glyAN-rnpA(sRNA) obtained in Example 1 and pSH32.

As a control, *E. coli* BL21 (DE3), transformed with the plasmid pACYC184 and pSH32, was used. Each of the transformed strains was seeded into 10 ml of an LB liquid medium (tryptone 10 g/L, yeast extract 5 g/L, and NaCl 5 g/L) (containing 34 mg/L of chloramphenicol, 25 mg/L of kanamycin and 1% arabinose) and shake-cultured at 25° C. and 220 rpm. Next, each of the strains was shake-cultured under the above-described medium conditions at 37° C. and 220 rpm. When the culture reached an $OD_{600}$ of 0.4, 1 mM IPTG was added to the medium to induce expression of the silk protein gene. At 4 hours after induction of the expression, the culture was sampled and centrifuged at 4° C. and 10,000 g for 10 minutes to obtain cell pellets, and RNA was extracted from the cell pellets.

For RNA extraction, 1 ml of Trizol was added to the cell pellet, after which the cell pellet solution was stirred for 1 minute and allowed to stand at room temperature for 5 minutes. Next, chloroform in an amount equal to 20% of the total volume was added to the cell pellet solution which was then stirred for 15 seconds and centrifuged at 13,000 rpm for 15 minutes. The produced supernatant was transferred into a fresh tube, and the same amount of isopropanol was added thereto and carefully stirred. Then, the mixture was centrifuged at 13,000 rpm for 30 minutes, and the supernatant was discarded. Next, 1 ml of 70% ethanol was added to the remaining material which was then centrifuged at 13,000 rpm for 5 minutes, and the above procedure was repeated again. Next, the resulting material was dried at room temperature and dissolved in 30 μl of RNase-free distilled water. In order to replace the extracted RNA with complementary DNA (cDNA), qPCR was performed using Rocketstrip (Bioneer, Korea). The extracted RNA was adjusted to 500 ng, and 2 μl of dN9 primer was added thereto. Then, the reaction mixture was adjusted to a total volume of 20 μl using RNase-free distilled water. The PCR reaction was performed under the following conditions: initial annealing at 30° C. for 150 seconds, cDNA synthesis at 60° C. for 1 hour, and then heat inactivation at 95° C. for 300 seconds.

To perform RT-PCR using the prepared cDNA, a reaction mixture having a total volume of 20 μl contained 8 μl of RNase-free distilled water, 10 μl of SYBR Green Mastermix (Enzynomics, Korea), 1 μl of a ¹⁄₁₀ dilution of the cDNA, and 0.5 μl of each primer. The RT-PCR reaction was performed under the following conditions: initial activation at 95° C. for 10 minutes, and then 45 cycles, each consisting of denaturation at 95° C. for 30 sec, annealing at 60° C. for 30 sec, and extension at 72° C. for 30 sec. To determine the melting curve, the temperature was increased from 55° C. to 95° C. by 0.5° C., and the reaction mixture was maintained at each temperature for 5 seconds.

Figure 6:
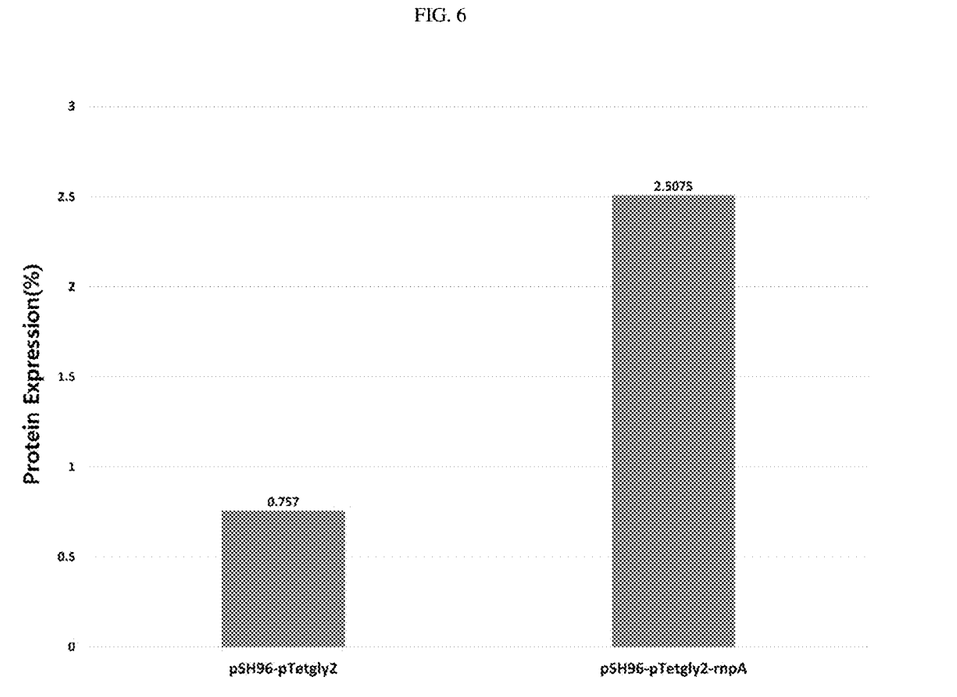
FIG. 6 is a graph showing the results of examining whether the level of intracellular mRNA is increased by reducing expression of the rnpA gene.

As a result, as shown in FIG. 6, in the case of cells in which expression of ribonuclease P (RnpA) was reduced, the level of mRNA was 24-fold higher than that in the control. This suggests that the degradation of mRNA is prevented by reducing expression of ribonuclease P (RnpA).

Example 5: Examination of Increase in Spider Silk Protein Production by Fed-Batch Fermentation The strain transformed with the plasmid pSH96 and pACYC184-rnpA(sRNA), constructed in Example 3, was cultured by fed-batch fermentation, and an increase in protein production in the strain was examined.

Figure 7A:
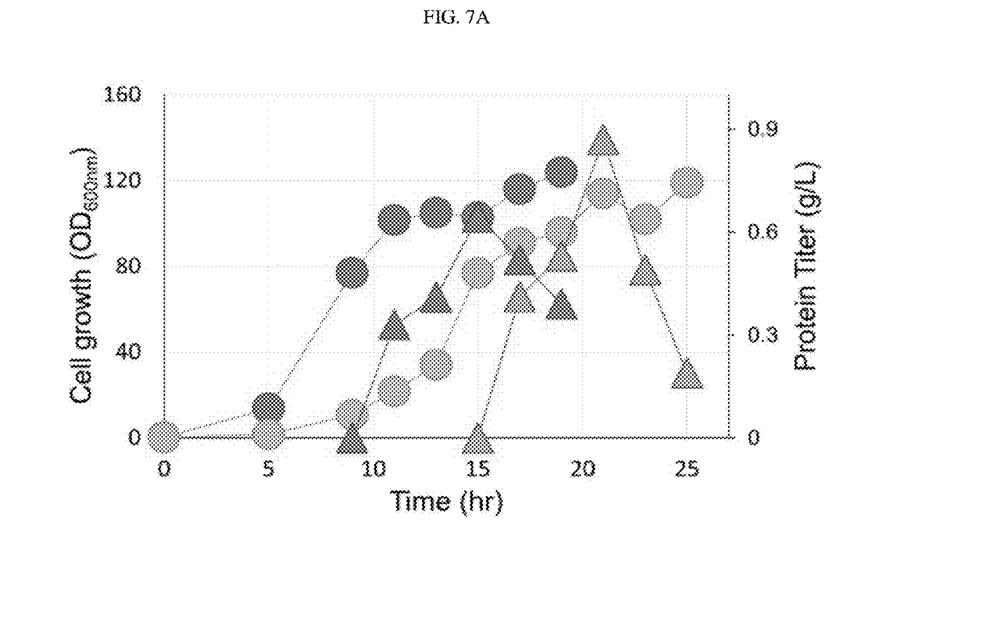
FIG. 7A is a graph showing the amount of a silk protein consisting of 96 repeats, produced by fed-batch culture.
Figure 7B:
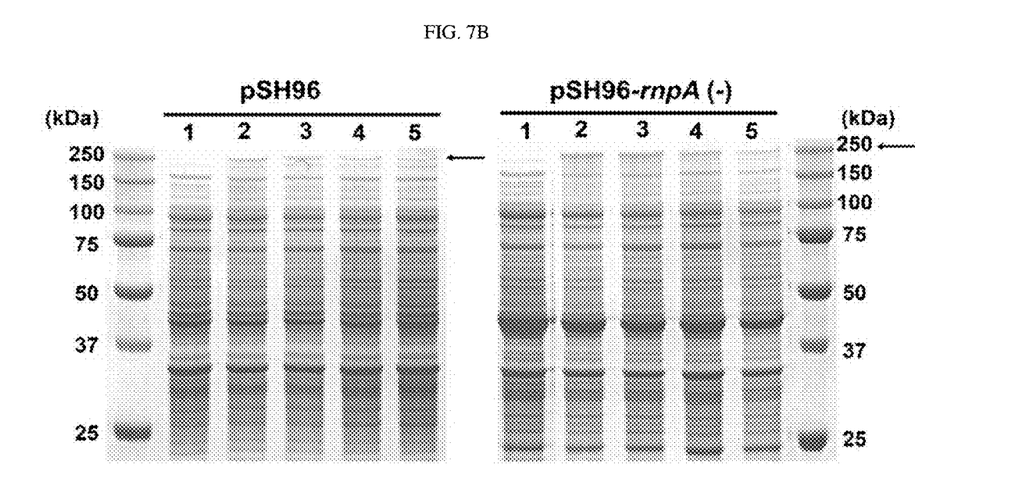
FIG. 7B shows the results of electrophoresis of the protein.

For fed-batch fermentation, a 6.6-L fermentor (Bioflo 3000; New Brunswick Scientific Co.) was used, and 1.6 L of R/2 medium, 10 g/L of glucose, 0.7 g/L of $MgSO_4 \cdot 7H_2O$, and an antibiotic (50 μg/mL kanamycin and/or 35 μg/mL chloramphenicol) were added to the strain in the fermentor. To adjust the dissolved oxygen level to 40%, air saturation was adjusted while the agitation speed was increased to 1000 rpm. A feeding solution was composed of 700 g/L of glucose and 20 g/L MgSO$_4$.7H$_2$O, and the pH of the culture was adjusted using 28% (v/v) ammonia solution. When the OD$_{600}$ reached about 70, 1 mM IPTG was added to the culture to induce protein expression. For 8 hours after induction of the expression, the culture was sampled at 2-hour intervals. Cell proliferation and the concentration of the protein obtained are shown in FIG. 7. As can be seen in FIG. 7, the protein could be obtained at a concentration of 0.9 g/L, which was 30% higher than the previously known concentration (0.7 g/L).

Example 6: Examination of the Increase in Expression of Other Proteins by Reduction in Expression of rnpA Gene Using the system for reducing rnpA gene expression according to the present invention, expressions of the gene (sfcA, SEQ ID NO: 6) encoding malic enzyme, the gene (srtA, SEQ ID NO: 7) encoding sortase A, the gene (cat2, SEQ ID NO: 8) encoding 4-hydroxybutyrate coenzyme A transferase and the cytochrome P450 gene (CYP73A5; cinnamate 4-hydrosylase: SEQ ID NO: 9 and CYP98A3: SEQ ID NO: 10) were analyzed, in addition to expression of the gene encoding silk protein. The Sortase A gene was synthesized by Bioneer (Korea), and the sfcA, cat2, CYP73A5 and CYP98A3 genes were obtained by PCR using the following primers.

```
sfcA_F:
                                        (SEQ ID NO: 11)
5'-CCATGGATATTCAAAAAAGAGTGAGT-3' sfcA_R:
                                        (SEQ ID NO: 12)
5'-TCTAGATTAGATGGAGGTACGGCGGTA-3'

Cat2_F:
                                        (SEQ ID NO: 13)
5'-GAATTCATGGAGTGGGAAGAGATATATA-3'

Cat2_R:
                                        (SEQ ID NO: 14)
5'-GGTACCCTAAAATCTCTTTTTAAATTCATT-3'

CYP73A5_F:
                                        (SEQ ID NO: 15)
5'-GCGAAGCTTACAGTTCCTTGGTTTCATAA-3'

CYP73A5_R:
                                        (SEQ ID NO: 16)
5'-GTACATATGATGGACCTCCTCTTGCTGG-3'

-continued
CYP98A3_F:
                                        (SEQ ID NO: 17)
5'-GGATCCATGTCGTGGTTTCTAATAGC-3'

CYP98A3_R:
                                        (SEQ ID NO: 18)
5'-GAATTCTTACATATCGTAAGGCACGC-3'
```

RnpA sRNA (SEQ ID NO: 1) and each of the sfcA, srtA and cat2 genes were inserted into pET30a (+)(Addgene, USA) and pTac15k (Addgene, USA) respectively to obtain recombinant vectors. Each of the vectors was transformed into an E. coli BL21 (DE3) strain. As a control, a strain transformed with a vector obtained by inserting each of the sfcA, srtA and cat2 genes into pET30a and pTac15k was used.

Each of the transformed strains was seeded into 10 ml of an LB liquid medium (tryptone 10 g/L, yeast extract 5 g/L, and NaCl 5 g/L) (containing 34 mg/L of chloramphenicol, 25 mg/L of kanamycin and 1% arabinose) and shake-cultured at 25° C. and 220 rpm. Next, each of the strains was shake-cultured under the above-described medium conditions at 37° C. and 220 rpm. When the culture reached an OD$_{600}$ of 0.4, 1 mM IPTG was added to the medium to induce expression of each protein. At 4 hours after induction of the expression, the culture was sampled and centrifuged at 4° C. and 10,000 g for 10 minutes to obtain cell pellets. The cell pellets were dissolved in TE buffer and 5× Laemmli sample buffer. The same amount (0.024 mg) of the sample was separated on 10% SDS-PAGE gel and stained with Coomassie brilliant blue R250 (Bio-Rad, USA) solution.

Figure 8:
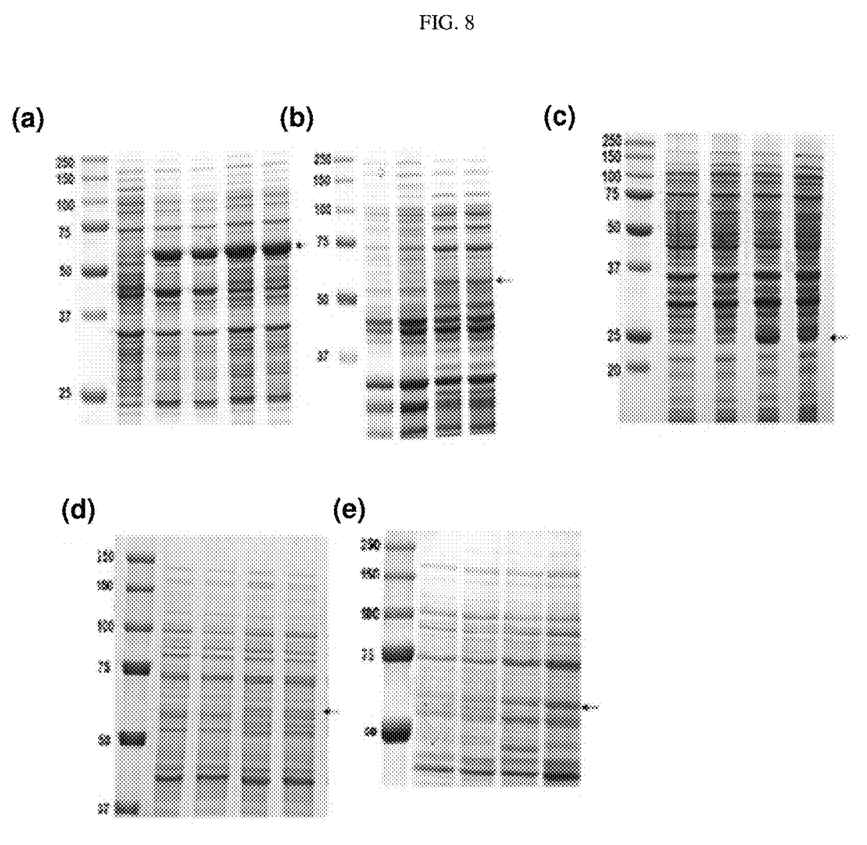

As a result, as can be seen in FIG. 8 (see electrophoresis images (a) through (e) therein), the expression levels of malic enzyme, sortase A, 4-hydroxybutyrate coenzyme A transferase (Cat2) and cytochrome P450 (cinnamate 4-hydrosylase and CYP98A3), expressed together with the RnpA sRNA, were significantly higher than the expression levels of the proteins expressed in the absence of the RnpA sRNA.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

According to the present invention, expression of a target protein, particularly a difficult-to-express protein having a high molecular weight can be dramatically increased by reducing expression of the rnpA gene so that the present invention is useful for increasing the productivity of proteins.

The invention claimed is:

1. A recombinant vector for expressing a target protein, which comprises a gene encoding the target protein and an sRNA against a gene encoding ribonuclease P, wherein the target protein is a difficult-to-express protein.

2. The recombinant vector of claim 1, wherein the sRNA is an sRNA against an Ribonuclease P Protein Component (rnpA) gene.

3. The recombinant vector of claim 2, wherein the sRNA has a nucleotide sequence of set forth in any one of SEQ ID NOs: 1 to 3.

4. The recombinant vector of claim 1, wherein the target protein is selected from the group consisting of silk proteins, antibodies, cytochromes, enzymes, and sortase A.

5. A recombinant microorganism into which the recombinant vector of claim 1 is introduced.

6. A recombinant microorganism into which a gene encoding a target protein and an sRNA against a gene encoding ribonuclease P are introduced, wherein the target protein is a difficult-to-express protein.

7. The recombinant microorganism of claim 6, wherein the sRNA is an sRNA an Ribonuclease P Protein Component (rnpA) gene.

8. The recombinant microorganism of claim 6, wherein the sRNA has a nucleotide sequence of set forth in any one of SEQ ID NOs: 1 to 3.

9. A method for producing a target protein, the method comprising the steps of:
   (a) expressing the target protein in the recombinant microorganism by culturing the recombinant microorganism of claim 6; and
   (b) recovering the expressed target protein.

10. A method for producing a target protein, the method comprising the steps of:
    (a) expressing the target protein in the recombinant microorganism by culturing the recombinant microorganism of claim 5; and
    (b) recovering the expressed target protein.

* * * * *

UNITED STATES PATENT AND TRADEMARK OFFICE
CERTIFICATE OF CORRECTION

PATENT NO.      : 10,351,890 B2
APPLICATION NO. : 15/533273
DATED           : July 16, 2019
INVENTOR(S)     : Sang Yup Lee Page 1 of 1

It is certified that error appears in the above-identified patent and that said Letters Patent is hereby corrected as shown below:

On the Title Page

Column 2 – OTHER PUBLICATIONS:
Line 36 Olson citation – "pp. 113" should be -- pp. 1-13 --.
Line 42 Turrini citation – "pp. 112" should be -- pp. 1-12 --.

Signed and Sealed this
Tenth Day of September, 2019

Andrei Iancu
*Director of the United States Patent and Trademark Office*